United States Patent [19]

Greenberg et al.

[11] Patent Number: 5,103,408
[45] Date of Patent: Apr. 7, 1992

[54] APPARATUS AND METHOD FOR DETERMINING THE ABILITY OF AN INDIVIDUAL TO PERFORM A TASK

[75] Inventors: Howard L. Greenberg, Huntington Beach; Samuel Moise, Los Gatos, both of Calif.; Robert D. O'Donnell, Dayton, Ohio; Ensor Rodriguez, San Marino, Calif.

[73] Assignee: Atlantic Richfield Company, Los Angeles, Calif.

[21] Appl. No.: 465,271

[22] Filed: Jan. 16, 1990

[51] Int. Cl.$^5$ .................. G06F 15/20; G06F 15/42
[52] U.S. Cl. .................. 364/550; 128/745; 434/323; 364/400
[58] Field of Search .................. 364/400, 401, 413.01, 364/413.02, 413.04, 413.27, 419, 550, 578, 410; 434/65, 322, 323, 333, 336, 362; 128/731, 745, 746

[56] References Cited

U.S. PATENT DOCUMENTS

| | | | |
|---|---|---|---|
| 2,678,692 | 5/1954 | Ranseen | 128/745 |
| 3,546,791 | 12/1970 | Koos et al. | 434/323 |
| 3,811,116 | 5/1974 | Takeuchi et al. | 364/413.02 |
| 3,901,215 | 8/1975 | John | 128/731 |
| 4,166,452 | 9/1979 | Generales, Jr. | 128/745 |
| 4,486,180 | 12/1984 | Riley | 434/323 |
| 4,541,806 | 9/1985 | Zimmerman et al. | 434/362 |
| 4,671,772 | 6/1987 | Slade et al. | 434/322 |
| 4,723,625 | 2/1988 | Komlos | 128/745 |
| 4,750,888 | 6/1988 | Allard et al. | 434/65 |
| 4,854,329 | 8/1989 | Walruff | 128/745 |
| 4,948,371 | 8/1990 | Hall | 364/410 |
| 4,950,167 | 8/1990 | Harris | 434/322 |
| 4,978,303 | 12/1990 | Campbell | 364/413.02 |

OTHER PUBLICATIONS

Systems Technology, Inc. Paper No. 288, "Using Rewards and Penalties to Obtain Desired Subject Performance", Marcia Cook et al., Jun. 1981.
Systems Technology, Inc. Paper No. 353, "A Manual Control Test for the Detection & Deterrence of Impaired Drivers", Anthony C. Stein et al., Jun. 1984.
Systems Technology, Inc. Paper No. 433, "The Driving Task, Driver Performance Models & Measurements", R. Wade Allen, et al., Jun. 1987.
Systems Technology, Inc. Paper No. 433, "Low Cost, Real Time Simulation Based on IBM-PC$^c$ Compatible Computers", R. Wade Allen et al., Jan. 1989.

Primary Examiner—Kevin J. Teska
Attorney, Agent, or Firm—Robbins, Dalgarn, Berliner & Carson

[57] ABSTRACT

An apparatus and method for testing individuals to determine their capability of conducting predetermined tasks. A base line is generated which is unique to each individual to whom the test is to be presented. The individual's current response to the battery of tests is compared by using an algorithm with the individual's base line to determine impairment of the individual. The algorithm is statistically designed to pass individuals relative to their base line performance level while eliminating all false negatives. When an individual tests positive, the test is repeated one or more times and the results compared using an algorithm which is statistically designed to pass individuals relative to their individual base line performance levels while eliminating all false positives. Such is accomplished by providing a source of images randomly and non-repetitively to a screen for recognition and response by the individual being tested. The responses are recorded in a compiler means and then compared to the previous results of the same individual which are stored in a data base and then tabulated to provide an output signal indicative of the individual's present ability to perform the task in question.

11 Claims, 4 Drawing Sheets

APPARATUS AND METHOD FOR DETERMINING THE ABILITY OF AN INDIVIDUAL TO PERFORM A TASK

FIELD OF THE INVENTION

The present invention relates generally to testing of individuals and more particularly to the testing of such individuals by comparison of test results to a base line previously generated to thereby ascertain whether or not the subject individual is capable of performing a particular task.

BACKGROUND OF THE INVENTION

The effects of alcohol, drugs (both ethical and illegal), fatigue, stress, emotional disturbance and the like have long been known to degrade both the physical and mental performance of human beings. Such degradation of performance may, in critical tasks, result in catastrophic loss of life and/or property. For example, impaired performance of an airline pilot may result in improper response to unusual circumstances or aircraft attitudes leading to a crash of the aircraft thereby resulting in total destruction of the aircraft and often loss of life to both crew and passengers. Numerous examples of such occurrences may be found by reference to the National Transportation Safety Board (NTSB) reports on aircraft accidents, both in the general and commercial aviation fields.

Impaired functional capabilities of operators of other types of vehicles can also lead to similar results, for example, bus or truck drivers carrying cargo or passengers, the operators of vessels on the high sea carrying cargo or passengers and the like. In addition thereto, individuals who are operating complex or sensitive equipment may likewise make decisions or take actions which could result in the occurrence of a catastrophic event.

Many attempts have been made directed to intrusive and non-intrusive testing of individuals to ascertain whether or not their systems contain performance degrading substances. The testing of individuals in this manner has raised many legal, ethical and moral issues and in many instances is inadequate. Particularly, such testing will not disclose degradation due to emotional disturbance, stress, debilitation as a result of age or disease or the like.

Various other attempts have been made to test individuals on a non-intrusive basis or without the necessity of testing breath or urine samples. For example, U.S. Pat. No. 3,901,215 to Erwin Roy John entitled "METHOD OF TESTING THE SENSES AND COGNITION OF SUBJECTS" discloses a system which produces an electroencephaloqraph in response to predetermined stimuli Which response is then compared to the patient's evoked response at a base line condition to ascertain differences between the two. Any differences are automatically statistically analyzed by a computer to ascertain the significance thereof. Obviously, such apparatus requires complex sensors and a highly trained attendant to provide the stimuli to the individual and record the results emanating from the individual's brain, both to establish the base line and the response to the stimuli.

Other apparatus in the form of simulators (both automotive vehicle and aircraft) have been developed to test the capability of an operator to perform pre-selected critical tasks in advance of assuming positions to carry out such tasks. The simulators are typically programed in such a manner that the operator functions to perform tasks (driving/flying) which are normally performed in the day-to-day work of that individual. The test results are compared against proper (objective) responses expected of individuals in similar circumstances. Although such tests are generally effective, they do not compare that person's present capabilities of performance against that same person's previously established performance response abilities. Furthermore, such simulators, even the most simple ones, are relatively expensive and the utilization of them for such testing requires a substantial amount of time.

SUMMARY OF THE INVENTION

The process in accordance with the present invention includes measuring an individual's response to a first battery of randomly occurring mental tests and then comparing the results of the tests by using an algorithm which is statistically designed to pass individuals relative to predetermined performance level While eliminating all false negatives and then repeating the first test with respect to any individual who failed to pass said first test and designating individuals who fail to pass the first test and repetition of the first test as being substantially impaired at the time the test is performed.

The apparatus in accordance with the present invention includes means for providing a source of images coupled to a means for presenting the same to an individual in a random sequence with each of the images having a predetermined configuration. Means operable by the individual is provided to permit the individual to signal recognition of the predetermined configuration which recognition is then compiled in compiler means and is compared in a comparator means to previous results of the same individual in responding to previous presentations of said images to produce an output signal indicative of the individual's present ability to perform the task in question.

DETAILED DESCRIPTION

Figure 1:
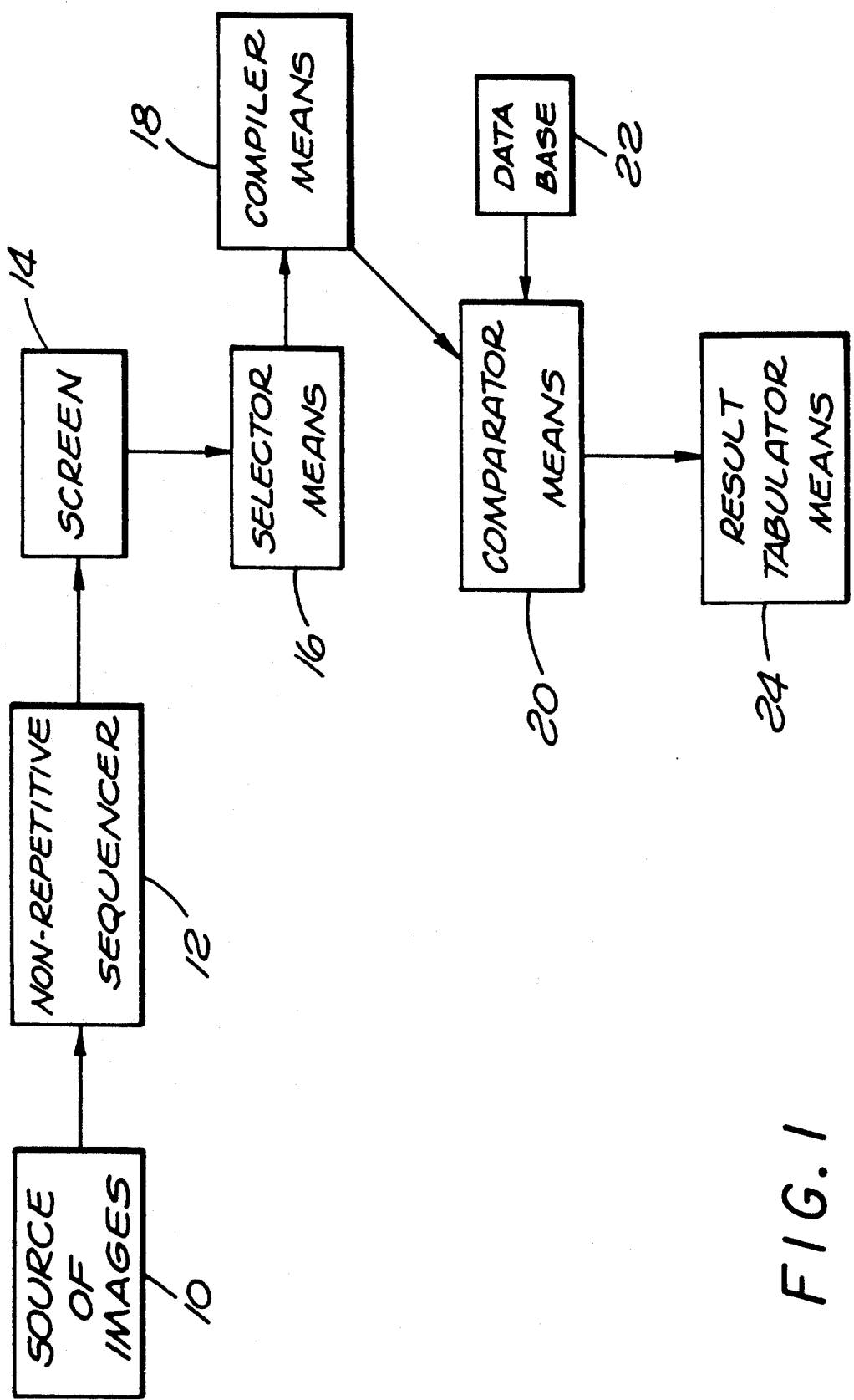
FIG. 1 is a block diagram illustrating apparatus utilized for testing individuals in accordance with the principles of the present invention.

Referring now more particularly to FIG. 1, there is disclosed in block diagram form an apparatus for administering and scoring tests given to individuals in accordance with the present invention. It is important that the images produced and presented to the individual being tested function to present the images on a non-repetitive random basis. It has been determined that reaction time of a subject is one of those parameters closely correlated with blood alcohol content as it affects performance on a flight simulator or similar apparatus. Therefore, it has been deemed important that the individual being tested (the subject) be able to react as quickly as possible upon recognizing the image to thus provide a response thereto. Therefore, a digital computer of the personal computer type including portable and/or lap top have been selected as the preferred manner in which the test is administered to the subject.

As is illustrated in FIG. 1, a computer may contain a source of images 10. The images may be audible or visual as desired and may take any particular form desired. In the preferred embodiment of the present invention, it has been determined that the source of images 10 would include a manikin (in the form of a stick figure) standing on a platform holding a box of different shape in each hand with a box in the platform having the shape of one of those held in the hand and with a symbol therein if desired. In addition, at the same time there will be presented two letters (Posner). An arrow will exist between the manikin and the letters and will point to the test to be conducted at that moment. The subject is then required to respond to the arrow in accordance with instructions previously presented. The manikin may take various positions and the letters may be different or the same. These images are presented on the computer screen 14 after passing through a non-repetitive sequence 12. That is, the images generated by the source 10 are sequenced in a random non-repetitive manner and presented on the screen 14 for recognition by the subject.

The non-repetitive random sequencing is important to eliminate the subject's ability to memorize the sequence in which images might be presented to thereby enhance his or her ability to score well on the test.

A selector means 16 is provided to the subject to allow the subject to react to the images being presented sequentially upon the screen 14 and respond thereto in accordance with the instructions previously represented. The selector means may be any type of device which may be quickly and easily manipulated by the subject to indicate a recognition of the images presented upon the screen 14. By way of simplifying apparatus and to use equipment familiar to most individuals at the present time, the standard terminal used on personal computers is preferred. Selected keys are depressed in accordance With instructions presented to the subject indicating a response to recognition of the images appearing on the screen. The responses to the images provided by the subject are received by a compiler means 18. The selector means 16 and the compiler means 18 also generate additional information measuring various parameters of response by the subject. For example, the reaction time of the subject may be measured with respect to recognition of the letters (the Posner test) test, the reaction time to the manikin test, the percent correct of the Posner and the manikin, the transition latency as to the Posner and the manikin and the transition percent correct between the Posner and the manikin. Other parameters may also be measured and may or may not be used in ascertaining the capability of the subject to perform the task in question.

The information accumulated by the compiler means 18 is then provided to a comparator means 20. The information may be utilized in a raw data sense or alternatively and more preferred, as will be discussed more in detail hereinafter, the raw data may be further manipulated, weighted or otherwise operated upon in accordance with the principles of the present invention to provide final information which may then be used to determine whether or not the subject has passed the test presented. The preferred means of making such a determination is to utilize a base line of information previously developed by and unique to the subject being tested which is retained in a data base 22. The base line results for the particular individual are then used by the comparator 20 to determine whether or not the subject is responding to the test in such a manner that the subject would be capable of performing the task under consideration at that particular time. This comparison is then tabulated in a tabulator means 24 with the result, i.e. pass or fail, with appropriate instructions attendant thereto presented upon the screen 14 for use by the subject.

Figure 2:
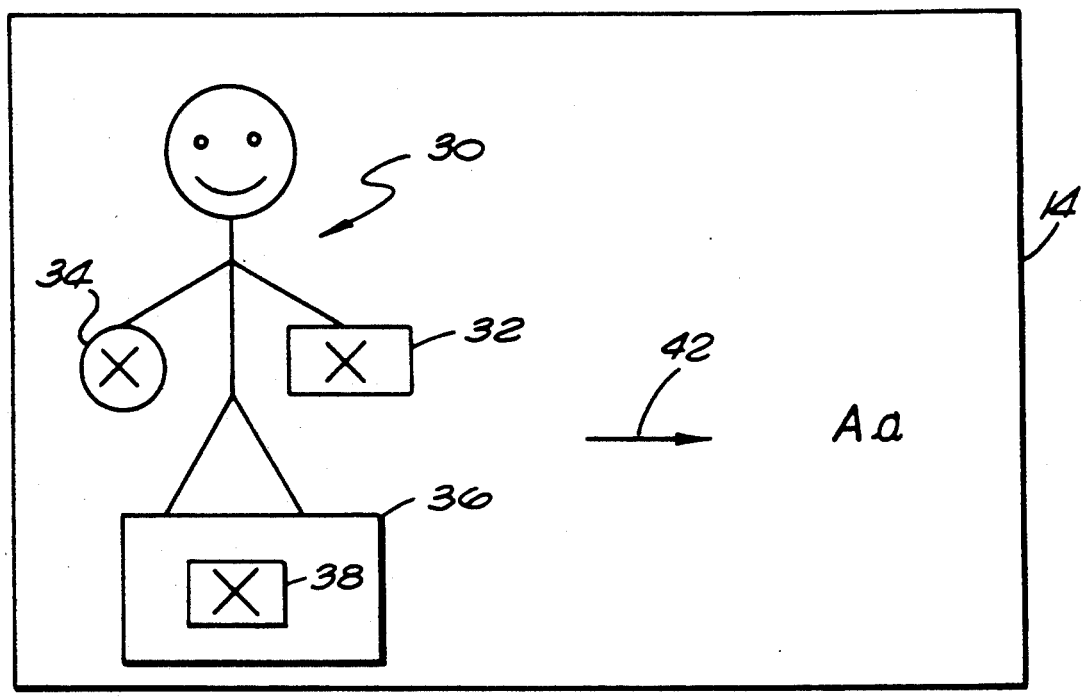
FIGS. 2 and 3 illustrate examples of visual images Which may be presented to an individual being tested in accordance with the principles of the present invention.
Figure 3:
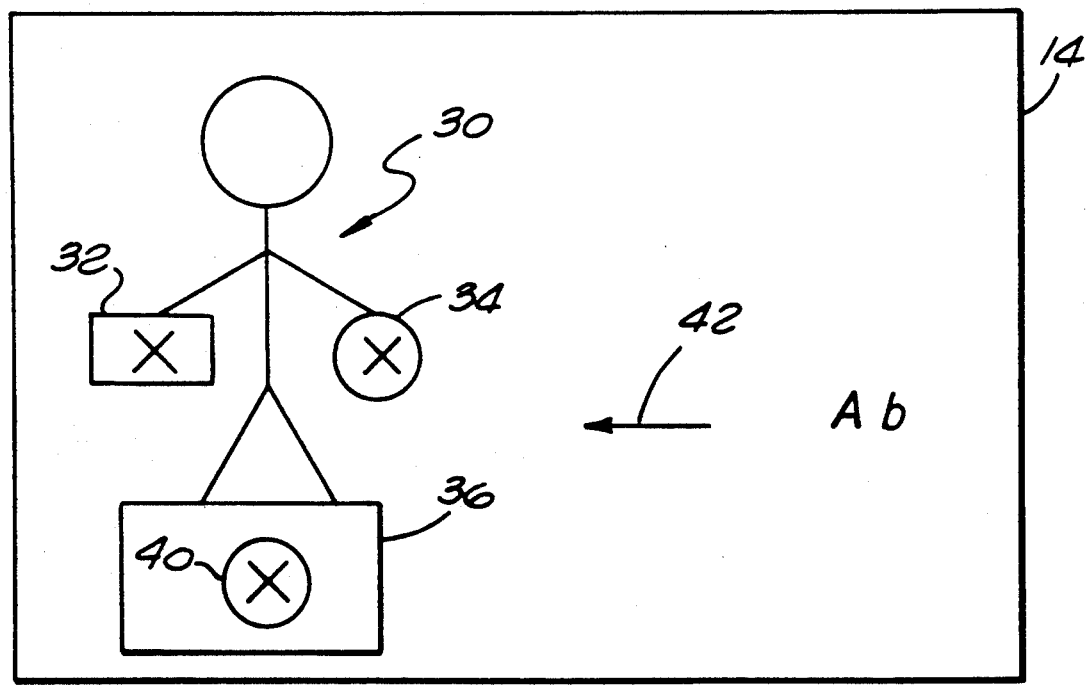

Referring now more particularly to FIGS. 2 and 3, there is illustrated schematically the images which would appear upon the screen 14. As is previously generally described, there is presented a manikin 30 which may be facing either toward the subject or away from the subject Facing toward the subject is as shown in FIG. 2 and away in FIG. 3 and is discerned by the eyes and smiling mouth on the face in the manikin 30 of FIG. 2. In each of the hands of the manikin, there is a box 32 or 34. The box may take various forms, such as the rectangle and circle respectively as illustrated in FIGS. 2 and 3. Although the rectangle is shown in the left and the circle in the right hand in each of FIGS. 2 and 3, it should be understood that this may vary from manikin to manikin. The manikin is standing upon a platform 36. Within the platform, there is a box 38 in FIG. 2 and 40 in FIG. 3 which will correspond in shape (not necessarily the same dimensions) to one of the boxes being held by the manikin. Each of the boxes may also contain a symbol, such as the X as illustrated in FIGS. 2 and 3, although such is not necessary.

On the right side of the screen, there appear two letters, (A and a) in FIG. 2 and (A and b) in FIG. 3. These letters may be any one of the alphabet or alternatively may be any other symbol desired, such as geometric symbols, arbitrary symbols, letter number combinations or the like. As above indicated, throughout the specification and claims these symbols will be referred to as the Posner test. Situated between the manikin and Posner test is an arrow 42. The arrow may point to either the Posner test or the manikin test. It is the mission of the test subject to first identify the direction in which the arrow is pointed, i.e. toward the Posner or toward the manikin. Once the test to be performed by the subject has thus been identified, the subject must then obey instructions which have previously been given and react to the images appearing on the screen 14 as quickly as possible.

Instructions to the subject may, for example, appear on the screen 14 as follows.

INSTRUCTIONS TO THE SUBJECT

On the screen, you will see 2 tasks presented simultaneously. In the middle of the screen is an arrow that will point to the task that is active on the current trial. You must perform the task to Which the arrow is pointing.

The task will start with a 2 minute warm-up period followed by the test session. The session will take approximately 5 minutes.

MANIKIN TEST

The task on the left side of the screen is the manikin. You will see an outline figure that can appear in various orientations. The figure will be holding a box in one hand and a circle in the other. The figure will be standing on a platform in which will be either a box or a circle. When this task is active, you are to determine which of the manikin's hands is holding the item that matches the item in the platform.

The response keys for this task are on the left side of the bottom row of keys on the keyboard. Press the key labeled "R" if the box is in the right hand, and press "L" if the box is in the left hand.

VERBAL THINKING

The task on the right side of the screen is the Verbal Thinking Task. You will see pairs of letters. When this task is active (the arrow points to the right side of the screen), you are to determine if the letters are the same or different. Same means that both letters are the same regardless of size of the letters. "Aa" and "AA" are both the same. Different means the letters are different, regardless of size, "Ab", "AB", "bA", "BA", "Ba" are all different.

The response keys for this task are on the right side of the bottom row of keys on the keyboard. Press the key labeled "s" if the letters are the same, and press the key labeled "D" if the letters are different.

It will be obvious to those skilled in the art that any number of images may be presented to the subject for each test depending upon the particular task to be performed and the results desired. In accordance with the preferred embodiment of the present invention, seventy-five such images as appear in FIGS. 2 and 3 are presented to the subject. As above described, the subject then responds to both the arrow 42 and recognition of the Posner test or the manikin test as above outlined. Each time the image is presented and reacted to by the subject, the selector and compiler means 16 and 18 measure the correctness and the reaction time of the subject to the test being presented.

The base line against which the results are measured at the completion of the test is unique for each individual being tested. That is, the subject may have assigned a unique identification number or may use a number already in existence, such as employee identification number, social security number or the like. Each subject to whom the test is to be administered, must perform the test a predetermined number of times over a predetermined time period in order to establish the base line against which future test results will be measured. For purposes of the test as above described in conjunction with FIGS. 2 and 3, it has been determined that a base line for a particular subject may be established after six test sessions have been administered. As presently understood, it has also been determined that these six tests should be separated by some specified term in accordance with t he principles of distributed training as is well understood by those skilled in the art. At the present time, it is believed preferable to administer each of the six tests on six successive days. It is, however, believed that this time interval may be contracted somewhat and still conform to the principles of the present invention. Over the long period of time, the base line for each individual includes only the last test sessions performed in excess of six and up to a maximum of thirty, that is, the base line will never include more than the last thirty test sessions administered to the subject (if there are that many) prior to the current test being administered. It can thus be seen that the base line data for each individual subject stored in the data base 22 is a constantly variable base line depending upon the results from each of the past sessions. It should be further understood that the base line includes only those tests which the subject has passed. In the event the subject fails the test, the fact of failure is recorded in the subject's historical data but the failed results are not included as part of the base line calculation, thus, the base line always contains passed tests data from the previous tests taken (at least six and a maximum of 30) and is calculated independently each time the subject is tested.

Subsequent to receiving the raw data and compiling the same as above described, the data is operated upon by selecting predetermined variables and establishing parameters for utilization in determining whether or not the subject is capable of performing the task in question. The parameters selected in accordance with the principles of the present invention, and as presently preferred, are an adjusted reaction time with respect to the manikin, the percentage correct of the total transitions, that is, shifting between the manikin and the Posner, and the raw manikin reaction time. The adjusted reaction time is calculated by dividing the manikin reaction time (in milliseconds) by the proportion correct (that is, the total number of manikin presentations selected which were correct divided by the total number of manikin presentations). The total transitions percent correct is determined by dividing the total transitions selected Which are correct by the total transitions, multiplied by one hundred. The raw manikin reaction time is given in milliseconds and is measured from the time the manikin is presented until the subject has selected the answer he or she desires in response to the image presented. Each of the parameters above described is then compared in the comparator means 20 to the base line average for each of these parameters and a difference therebetween is determined, that is, the average adjusted reaction time for the manikin on the current test is compared with the average adjusted reaction time already existing in the base line and the difference is determined. The differences thus determined are then weighted pursuant to a Deviation Weights for Composite Measures table as follows:

| DEVIATION WEIGHTS FOR COMPOSITE MEASURES | | |
| --- | --- | --- |
| ADJUSTED RATE MANIKIN | TOTAL TRANSITIONS PERCENT CORRECT | MANIKIN REACTION TIME (MILLISECONDS) |
| 0–50 = 0 | | 0–50 = 0 |
| >50 = 1 | ≦ − 1.0 = 1 | >50 = 1 |
| >150 = 2 | ≦ − 2.5 = 2 | >100 = 2 |
| >200 = 3 | ≦ − 4.0 = 3 | >150 = 3 |
| >300 = 4 | ≦ − 5.0 = 4 | >200 = 4 |
| >600 = 5 | ≦ − 7.5 = 5 | >300 = 5 |
| >1000 = 6 | | |

Thereafter the weighted numbers as determined from this comparison in the comparator means 20 are totaled. As can be seen from the above chart, the maximum total possible on any one pass is 16. That is, if the adjusted rate, manikin is greater than 1,000, then the weighted number is 6, if the total transitions percent correct difference is equal to or less than 7.5, the weighted number is 5 and if the total difference in manikin reaction time is greater than 300 milliseconds, then the weighted number is 5. The total of these three weighted number (5, 5 and 6) is therefore 16.

The total of the weighted numbers determined as above defined is then inserted into an algorithm to ascertain the subject's final test score. The algorithm is as follows: $FS = (1 - \Sigma/16) \times 100$. Where FS = Final Score and $\Sigma$ = total sum of the weighted numbers. Through utilization of this algorithm, there is obtained a score relative to 100 which ascertains whether or not the subject has passed. It has presently been determined that a passing test score is 75. Obviously, this may change depending upon the particular task to be performed and the manner in which the test is analyzed by those administering the test.

A principle purpose for administering the test is to maximize sensitivity as well as specificity. Sensitivity as used throughout the specification and claims means detecting someone who is really impaired, while specificity means that the test will only pass those who are false positives but not the others. In administering the test, it must be designed so that it cannot miss anyone on the first pass through the test who is in fact impaired. As a result of this, there will always be false positives which result from taking the test. Since this will occur, a mechanism has been instituted to enable a detection of those Who fail the test When it is first administered, but this failure is a false positive, that is, the individual is not really impaired but for some reason failed the test when it was administered. In order to detect these false positives, the subject who fails the test when it is first administered, has the test re-administered immediately following the failure. If after re-administration of the test, one or more times, the subject still fails the test, then it is determined that the individual is really impaired and should not be permitted to perform the task.

Obviously, the particular algorithm as above set forth is designed to filter the processing results obtained by the subjects taking of the test so as to determine the performance levels of the subject While eliminating all of the false negatives. The particular algorithm chosen is particularly pertinent to the parameters selected as above described. As a result, those skilled in the art will recognize that if different parameters are chosen or different means for weighting or otherwise manipulating the raw data obtained are utilized, then the algorithm may also change accordingly. It is, therefore, to be understood that any algorithm may be utilized which is statistically designed on the first pass through to pass individuals relative to the predetermined performance level (the passing score) while eliminating all false negatives, while at the same time filtering tho processing results (the data obtained by the subjects taking the test on subsequent passes after the first fail pass) and is statistically designed to pass individuals relative to the predetermined performance level (the passing score) while eliminating all false positives.

Figure 4:
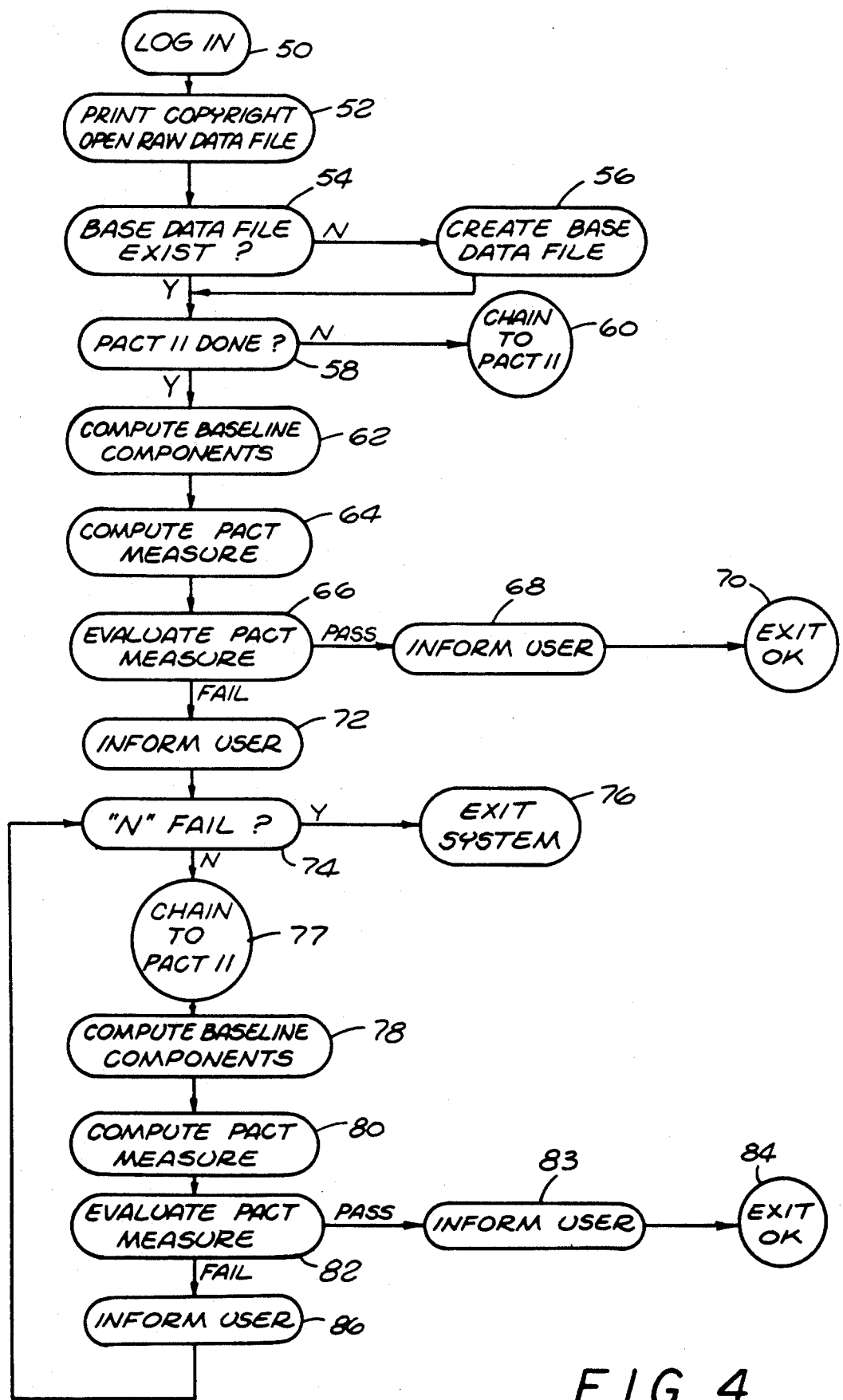
FIG. 4 is a flow chart illustrative of the steps performed in testing in accordance With the principles of the present invention.

By specific reference to FIG. 4, there is illustrated a flow chart for administering the test as above described utilizing a personal computer type digital computer apparatus as above generally described. As is shown in FIG. 4 at 50, the subject logs onto the computer system. Such is accomplished by entering the unique identification which is assigned to the particular subject being tested. Thereafter, the computer is programmed to automatically print the copyright notice as indicated at 52 and to open the raw data file for this particular subject. The computer then determines, as is illustrated at 54, whether or not a base line exists for this particular subject. If a base line does not exist, then the command to create a base data file is given as shown at 56 and thereafter the test is administered to the subject as explained above with the test results being accumulated until such a time that at least six passes have been made through the test thereby creating an appropriate base line.

If, on the other hand, the base data file with the appropriate base line does exist, then the system inquires as to whether or not the test has been administered. The name which has been arbitrarily given to the test for purposes of the flow chart, as illustrated in FIG. 4, is Pact 11. This designation means this is Pact Test 1 at Level 1. If the test has not been administered, then the command Chain to Pact 11 is given as is illustrated at 60. Chain to Pact 11 merely means that the test is administered by presenting the images 30 on the screen 14 in the random non-repetitive manner as above described. After the test is completed, the base line components are computed as is indicated at 62, that is, the averages of the last tests (more than six and up to thirty) are computed. Thereafter, as is illustrated at 64, the Weighted numbers are applied and summed and manipulated by the algorithm to ascertain the score obtained by the subject. The score is then evaluated as indicated at 66 by comparison to the base line components averaging and a determination is made as to whether or not the subject has passed or failed. If the subject has passed the test, then he or she is informed as indicated at 68 and is instructed to exit the system as is indicated at 70. If, however, the subject has failed the test, then the subject is informed as indicated at 72. The subject then has posed to he or she, as is indicated at 74, the question as to the number of the failure that is indicated by the "N" fail? If the number of times which the subject has failed the test at this particular sitting equals the number of failure times permitted as indicated by "N", then the yes answer leads to an exiting of the system as is indicated at 76. The number of times which a failure is permitted to occur will depend upon what is established by the administrators of the tests to be sure that a false positive exists and to eliminate the possibility of false negatives. If the answer to the question as how many failures have occurred is less than "N" failures, then as shown at 76, the system will assume a false positive and will re-administer the test, compute the base line results as shown at 78, compute the score as shown at so and evaluate the same as shown at 82 wherein if there is a pass, the user is informed and exiting of the system is appropriate as shown at 84. However, if a failure occurs, the user is informed at 86 With a return to the "N" fail at shown at 74 until "N" failures have occurred at which time the system will be exited as shown at 76 with instructions to the subject to contact his or her supervisor for further instructions. Obviously, if "N" failures have occurred, the subject is impaired and should not be permitted to attempt to perform the task in question at that particular time.

It is believed that appropriate "N" iterations of the test as above described, will, in all cases, detect those who are really impaired and will in all cases eliminate false negatives as well as all false positives. However, it should be understood that instead of repeating the Pact 11 Test one or more times as above suggested, one may alternatively test the subject after the failure of the Pact 11 Test by presenting to the subject one or more different additional tests to accomplish the same purpose.

Figure 5:
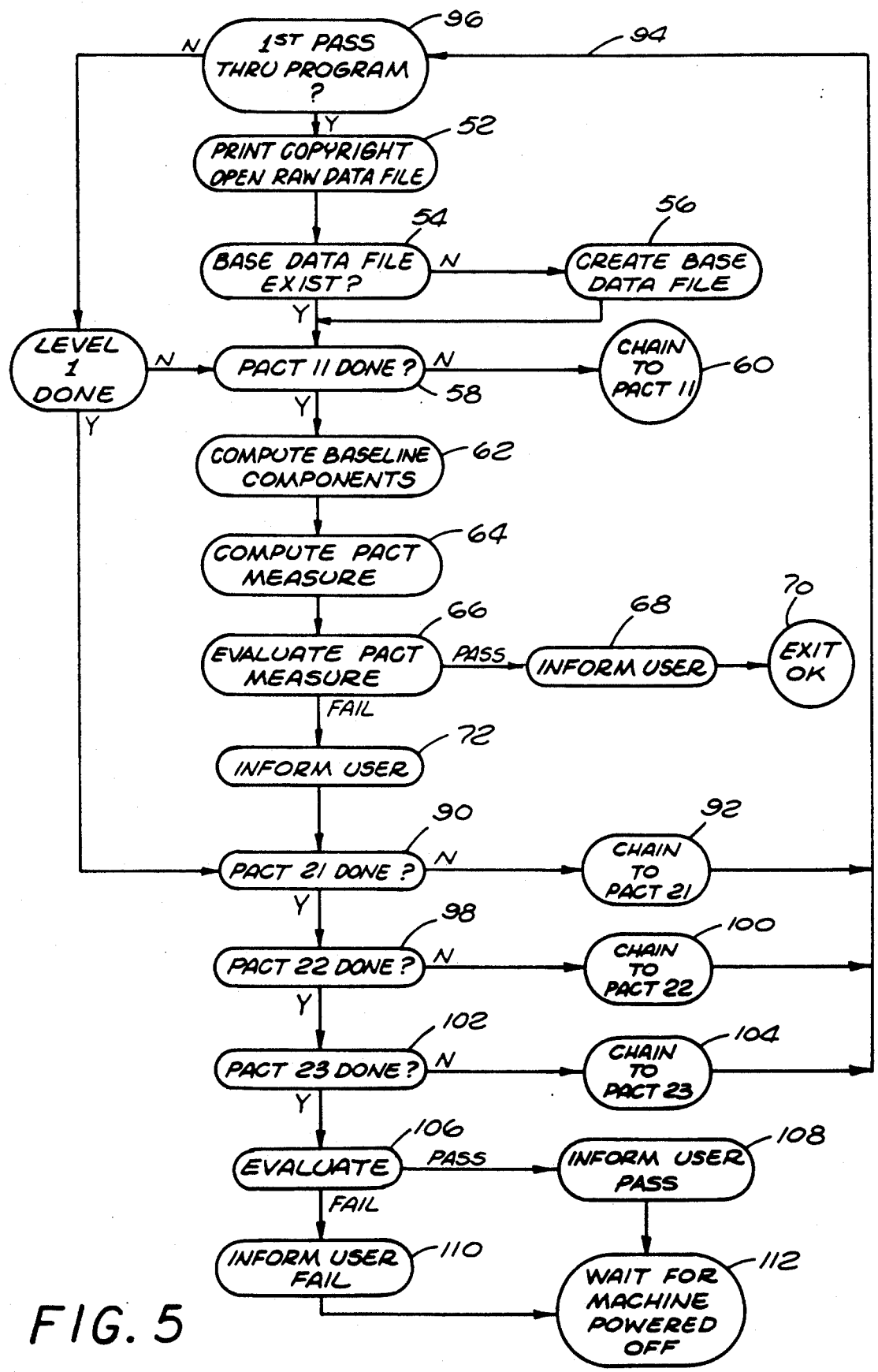
FIG. 5 is a second flow chart illustrative of an alternative embodiment of testing in accordance with the principles of the present invention.

A flow chart is illustrated in FIG. 5 designed to administer an additional test having three successively more difficult levels to a subject who fails the Pact 11 Test. As is shown in FIG. 5, several steps are identical to those in the flow chart shown in FIG. 4 and are so indicated by utilizing the same reference numerals.

In utilizing the system designed to operate in accordance with the flow chart of FIG. 5, once the subject logs in, as indicated in FIG. 4 at 50, the subject is asked whether or not this is his or her first pass through the program, that is, through this particular test. If the answer is yes, then the test is administered in precisely the same manner as indicated hereinabove with respect to entries 52 through 72. If the answer is no, then the subject is asked whether or not the Level 1 test, that is Pact 11, has been done. If the answer is no, then the Pact 11 Test is administered. If the answer is yes, then the system automatically inquires as to whether or not the second test Level 1 has been administered, as is indicated at 90. If the Pact 21 Test has not been administered, then the command would be to Chain to Pact 21 as indicated at 92. As with regard to the Pact 11 Test, this merely means that the Pact 21 Test, that is, second Pact Test at Level 1 would be administered to the subject. Although not shown in FIG. 5, there would be similar steps such as indicated at 62, 64 and 66 with regard to the Pact 11 Test Which Would apply insofar as the Pact 21 Test is concerned. Subsequent to completion of the Pact 21 Test, the system would automatically return as indicated by the line 94 to the first pass through program as indicated at 96. Upon indicating that this is not the first pass through the first program, the system would automatically revert to the question of whether or not Pact 11 had been administered and upon being advised that it has, step down to the Pact 21 done as shown at 90 would occur. Upon the indication that such had already occurred, the system would step to the Pact 22 done question as illustrated at 98. Upon an indication that the Pact 22 test had not been administered, then there would be an automatic stepping to Chain to Pact 22 as indicated at 100. Again, the test 2 at Level 2 would be administered utilizing similar computing and evaluating steps as indicated at 62 through 66 with regard to the Pact 11 Test. Again, upon completion of the Pact 22, a return to the first pass through the program at 96 would occur with the stepping down through Pact 21 and Pact 22 to Pact 23 as indicated at 102. Upon indicating that this test had not been administered, it would automatically administer the test by Chain to Pact 23 as indicated at 104. Upon completion thereof, again there would be the passing through the questions at 96 for first pass through the program and Whether or not Level 1 has been accomplished and then step through Pact 21, 22, 23 whereupon appropriate evaluation would occur utilizing the steps 62 through 66 as above indicated. This, however, would include the results of each of the tests Pact 21, Pact 22 and Pact 23 by an appropriate algorithm which could filter the processing results in such a manner as to eliminate all the false positives and false negatives while statistically being designed to pass individuals relative to a predetermined performance level as established by those administering the tests. If the subject passes the test, the subject would be informed and would then exit the system and perform the task in question. If the subject fails the test, the subject Would be informed and would be given appropriate instructions to report to his or her supervisor for further processing. The machine would then automatically power off as indicated at 112.

It should be obvious to those skilled in the art that it can be determined that if the subject passes the first level of the test 2 after the first test, then the subject is unimpaired and may be able to perform the task in question, that is, all three levels of the second test may not necessarily need to be done and may be administered only if upon evaluation of the test results, it is indicated that that particular level has resulted in a failure. That is, Pact 22 would only be administered to the subject upon a failure of Pact 21 and Pact 23 would only be administered upon a failure of Pact 22.

It should be understood by those skilled in the art that the foregoing flow charts and descriptions are representative only and not intended to restrict or limit the present invention as defined in the claims appended hereto.

What is claimed is:

1. Apparatus for determining the ability of a subject to perform a task comprising:
    (a) a source of randomly occurring images, each of said images having a predetermined configuration of at least two test tasks;
    (b) means coupled to said source for presenting sequentially said images from said source to said subject but in a manner such that the sequence of presentation thereof is non-repetitive;
    (c) means operable by said subject for providing a signal indicative of recognition by said subject of said predetermined configuration of each said image as sequentially presented;
    (d) compiler means intercoupled with said selector means for receiving said signals and compiling a list representative of correct recognition by said subject of said image predetermined configuration; and
    (e) comparator means coupled to said compiler means for comparing said list of correct image configuration recognition to previous sequential presentation of said images for producing an output signal indicative of said subject's present ability to perform said task.

2. A process for interactively determining the capability of a subject to perform a task comprising:
    (a) simultaneously presenting on a screen visually perceptible to said subject at least two test tasks;
    (b) presenting on said screen with said at least two test tasks an indicator directing said subject to that task to be performed;
    (c) changing said test tasks in a randomly occurring manner to provide a battery of test tasks;
    (d) providing said subject a means for responding to each said indicated test task within said battery of test tasks;
    (e) measuring said subject's response to each of said randomly occurring test tasks to obtain a current response;
    (f) filtering the results obtained in step (e) using an algorithm that is statistically designed to pass subjects relative to a predetermined performance level while eliminating all false negatives; and
    (g) designating subjects who pass the filtering operation in step (f) as being substantially non impaired at the time said battery of tests is taken.

3. A process as defined in claim 2 which further includes the steps of (h) repeating steps (a) through (e) with respect to any subject who fails to pass said battery of tests; (i) filtering the results obtained in step (h) using a second algorithm that is statistically designed to pass subjects relative to a predetermined performance level while eliminating all false positives; and (j) designating subjects who pass the filtering operations in steps (f) and (i) as being substantially non-impaired at the time said battery of tests is taken.

4. The process as defined in claim 2 wherein one of said at least two test tasks of step (a) is a letter recognition test and another of said at least two test tasks is a spatial orientation system.

5. The process as defined in claim 4 wherein said letter recognition test is a Posner test and said spatial orientation test is a manikin test.

6. A process as defined in claim 2 which further includes the steps of establishing a base line unique to each subject taking said test and comparing the current response of said subject to said subject's base line to ascertain said subject's current test results.

7. A process as defined in claim 6 wherein said base line for each subject is established by each said subject taking said battery of tests a predetermined number of times with each test taking session temporally separated from the previous test taking session by a predetermined time period.

8. A process as defined in claim 7 wherein said base line for each subject includes the results of all of said tests previously taken and passed subsequent to first establishing said base line by said subject up to a predetermined number.

9. A process for interactively determining capabilities of a subject to perform normal job functions comprising
 (a) simultaneously presenting on a screen visually perceptible to said subject at least two test tasks;
 (b) presenting on said screen with said at least two test tasks an indicator directing said subject to that task to be performed;
 (c) changing said test tasks in a randomly occurring manner to provide a battery of test tasks;
 (d) providing said subject a means for responding to each said indicated test task within said battery of test tasks;
 (e) measuring said subject's response to each of said randomly occurring test tasks to obtain a current response;
 (f) filtering the results obtained in steps (a) through (e) using an algorithm that is statistically designed to pass a subject relative to a predetermined performance level while eliminating all false negatives;
 (g) repeating the operation in steps (a) through (e) using a second more comprehensive battery of tests in respect to any subject who failed to pass said battery of tests;
 (h) filtering the results obtained in step (g) using a second algorithm that is statistically designed to pass a subject relative to a predetermined performance level while eliminating all false positives; and
 (i) designating individuals who pass the filtering operations in steps (f) and (h) as being substantially non-impaired at the time in question.

10. The process as defined in claim 9 wherein said second battery of tests includes a plurality of individual tests each differing from the other.

11. The process as defined in claim 10 wherein said subject is designated non-impaired after passing any one of said individual tests in said second battery of tests.

* * * * *